United States Patent [19]

Ballini

[11] Patent Number: 5,649,530

[45] Date of Patent: Jul. 22, 1997

[54] MICRONIZED DOUCHE DEVICE FOR CLEASING NASAL AND NEIGHBORING CAVITIES

[75] Inventor: Faustino Ballini, Bovezzo, Italy

[73] Assignee: Mefar S.p.A., Bovezzo, Italy

[21] Appl. No.: 610,536

[22] Filed: Mar. 4, 1996

[30] Foreign Application Priority Data

Mar. 14, 1995 [IT] Italy ................... MI95A0497

[51] Int. Cl.$^6$ .................................................. A61M 31/00
[52] U.S. Cl. .................................. 128/200.14; 604/35
[58] Field of Search ................. 128/200.13, 200.14,
128/200.19, 200.2, 200.21, 200.22, 204.13;
239/104, 106, 110, 119, 120, 203.12; 604/34,
35, 37, 58

[56] References Cited

U.S. PATENT DOCUMENTS 2,021,332  11/1935  Silten .
2,566,806  9/1951  Miller et al. .
3,522,806  8/1970  Szekely .
3,771,721  11/1973  Van Amerongen .
5,388,571  2/1995  Roberts et al. ............... 128/203.12

Primary Examiner—Vincent Millin
Assistant Examiner—Robert N. Wieland
Attorney, Agent, or Firm—Guido Modiano; Albert Josif

[57] ABSTRACT

A micronized douche device for cleansing nasal and neighboring cavities, including: a bell-shaped body that forms an atomizing chamber, a spray nozzle that is associated with a duct for feeding a cleansing liquid and with a compressed air injector. The spray nozzle is axially aligned with a hole for the outflow of the atomized stream of cleansing liquid. A port for the discharge of the cleansing liquid, with the removed secretions, is furthermore provided on the bottom of the atomization chamber.

6 Claims, 2 Drawing Sheets

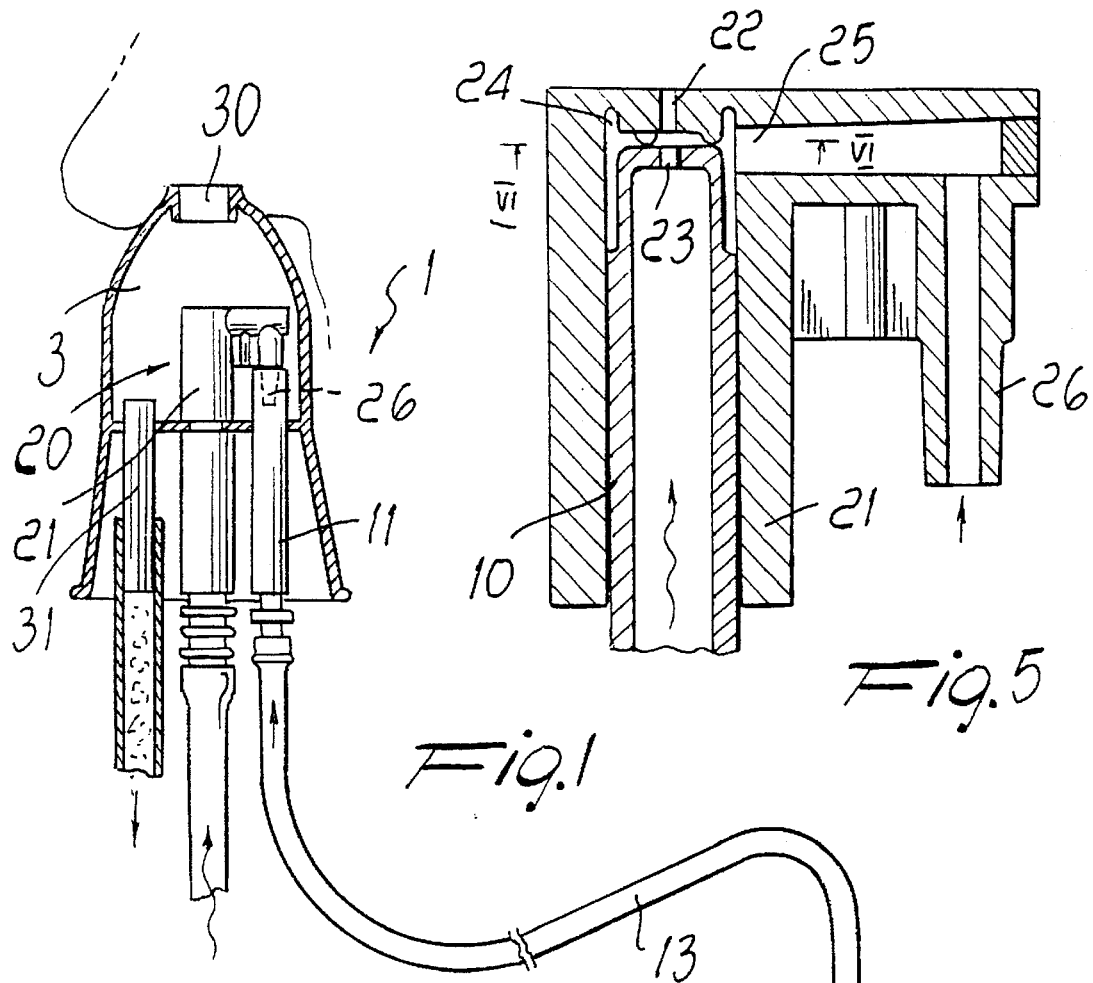
Fig.1
Fig.5
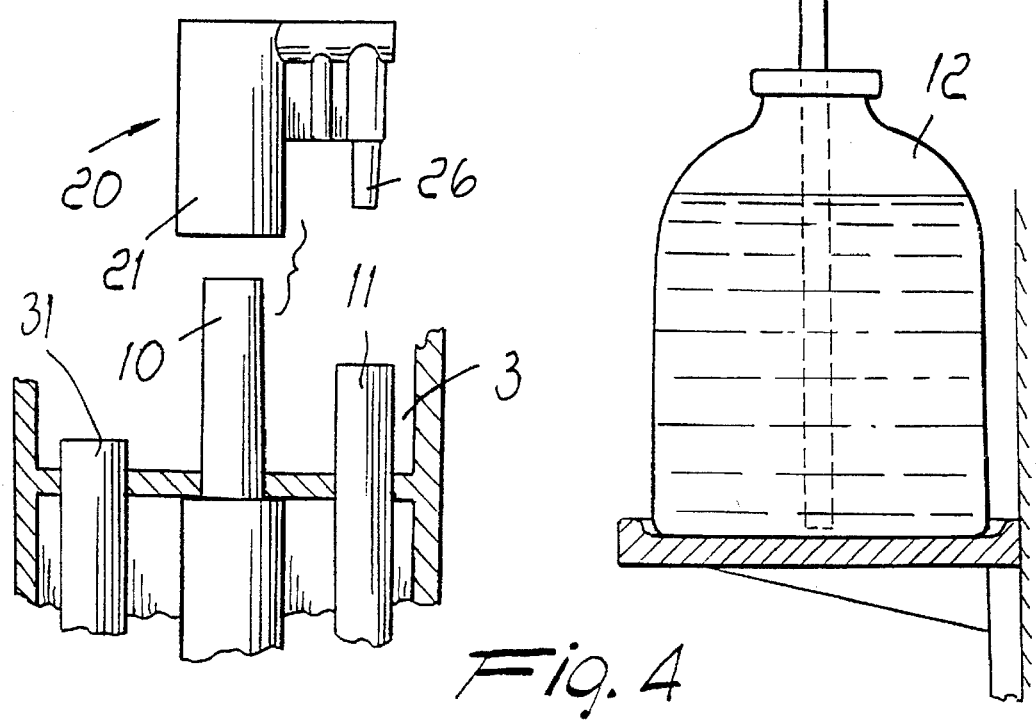
Fig.4

MICRONIZED DOUCHE DEVICE FOR CLEASING NASAL AND NEIGHBORING CAVITIES

BACKGROUND OF THE INVENTION

The present invention relates to a micronized douche device for cleansing nasal and neighboring cavities.

Italian patent application Serial No. MI 93A002386 of Nov. 9, 1993, the contents of which are incorporated herein by reference, discloses a micronized douche device using running water, for cleansing nasal and neighboring cavities, which is constituted by a bell-shaped body that forms an atomization chamber; a cleansing liquid containment tray is provided on the bottom of the chamber, and a spray nozzle draws from the tray, is associated with a compressed air injector, and is axially aligned with the outlet hole formed by the bell-shaped body.

A duct for the continuous introduction of the cleansing liquid leads into the chamber, and there is a discharge port that controls the level of the cleansing liquid inside the tray and allows to expel outside the excess cleansing liquid together with the secretions that have been removed.

Although this embodiment is extremely valid from all points of view, it entails drawing the cleansing liquid from the bottom of the chamber in which the removed secretions were introduced; accordingly, the removed secretions, by mixing with the cleansing liquid, could at least partially be drawn up again by the spray nozzle; therefore, an atomized jet which might be constituted not only by the cleansing liquid would possibly be dispensed.

Moreover, another problem is constituted by the fact that in order to feed the cleansing liquid into the atomizing chamber it is necessary to provide a positive pressure, so as to allow the cleansing liquid to enter the atomization chamber.

SUMMARY OF THE INVENTION

One principal aim of the invention is indeed to solve the above-described problems, providing a micronized douche device for cleansing nasal and neighboring cavities that allows to keep the cleansing liquid fed to the injector completely separate from the cleansing liquid that contains the removed secretions, which must be discharged externally, so that one is always certain that the atomized jet is constituted exclusively by the cleansing liquid, which usually is thermal water.

One particular object of the invention is to provide a micronized douche device that allows to introduce the cleansing liquid in the region of the injector without having to apply a positive pressure to feed the liquid.

Another object of the present invention is to provide a micronized douche device that is capable of giving the greatest assurances of reliability and safety in use by virtue of its particular constructive characteristics.

Another object of the present invention is to provide a micronized douche device that is structurally very simple and has a low cost, so that it is particularly adapted to be used as a disposable device.

According to a preferred aspect of the invention, there is provided a micronized douche device for cleansing nasal and neighboring cavities, which comprises a bell-shaped body that forms an atomizing chamber, and which is characterized in that it comprises a spray nozzle that is associated with a duct for feeding a cleansing liquid and with a compressed air injector. The spray nozzle is preferably axially aligned with a hole for the outflow of the atomized stream of cleansing liquid, and a port for the discharge of the cleansing liquid, with the removed secretions, is provided on the bottom of the atomization chamber.

BRIEF DESCRIPTION OF THE DRAWINGS

The particular characteristics and advantages of the invention will become apparent from the following detailed description of a preferred but not exclusive embodiment of a micronized douche device for cleansing nasal and neighboring cavities, which is described in the following text and illustrated in the accompanying drawings only by way of non-limitative example, wherein:

FIG. 1 is a schematic view of one preferred embodiment of the micronized douche device according to the invention;

FIG. 4 is a partially sectional exploded view of the inside of the bell-shaped body and of the connecting element of the device;

FIG. 5 is a sectional view, taken along an axial plane, of the connecting element associated with the air injector of the device.

DESCRIPTION OF THE PREFERRED EMBODIMENTS

Figure 6:
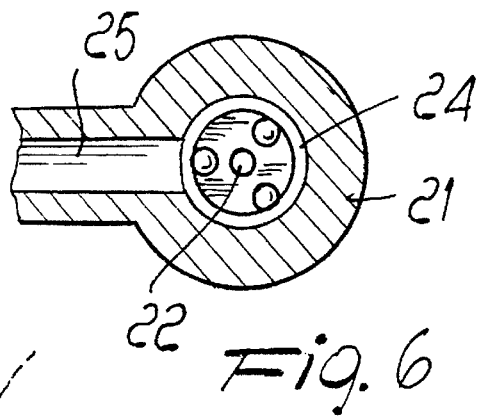
FIG. 6 is a sectional view, taken along the plane VI—VI of FIG. 5.
Figure 2:
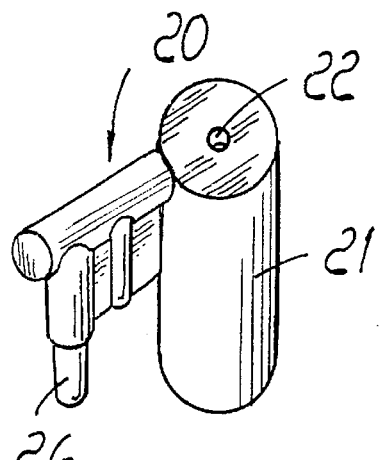
FIG. 2 is a perspective view of the element for connecting the compressed air injector and the cleansing liquid feed duct of the device of FIG. 1.

With reference to the above figures, a preferred embodiment of a micronized douche device with continuous operation using running water for cleansing nasal and neighboring cavities, generally designated by the reference numeral 1, comprises a bell-shaped body 2 that internally forms an atomization chamber 3.

A compressed air injector, designated by the reference numeral 10, is provided at the bottom of the atomization chamber 3 and is connected to an external unit for supplying compressed air.

A duct 11 for introducing a cleansing liquid is provided to the side of the injector 10; the cleansing liquid can be advantageously constituted by thermal water that is contained in a container or bottle 12 that is connected to the duct 11 by means of a tubular element 13.

An important particularity of the invention is constituted by the fact that there is a connecting element 20 that connects the injector 10 to the inlet duct 11.

More specifically, the connecting element 20 is provided with a sleeve 21 that fits over the injector 10 so as to provide a hermetic coupling.

A spray nozzle 22 is provided at the end that lies opposite to the open end of the sleeve 21; the nozzle 22 is formed in axial alignment with an injection hole 23 formed by the injector 10 and at an annular chamber 24 into which a branching duct 25 enters radially; the duct 25 is associated with a coupling 26 that is inserted in the inlet 11.

With this arrangement, therefore, the cleansing liquid that arrives from the container 12 is drawn by a Venturi effect into the chamber 24 and is fed therefrom into the atomization chamber in the form of an atomized jet.

Figure 3:
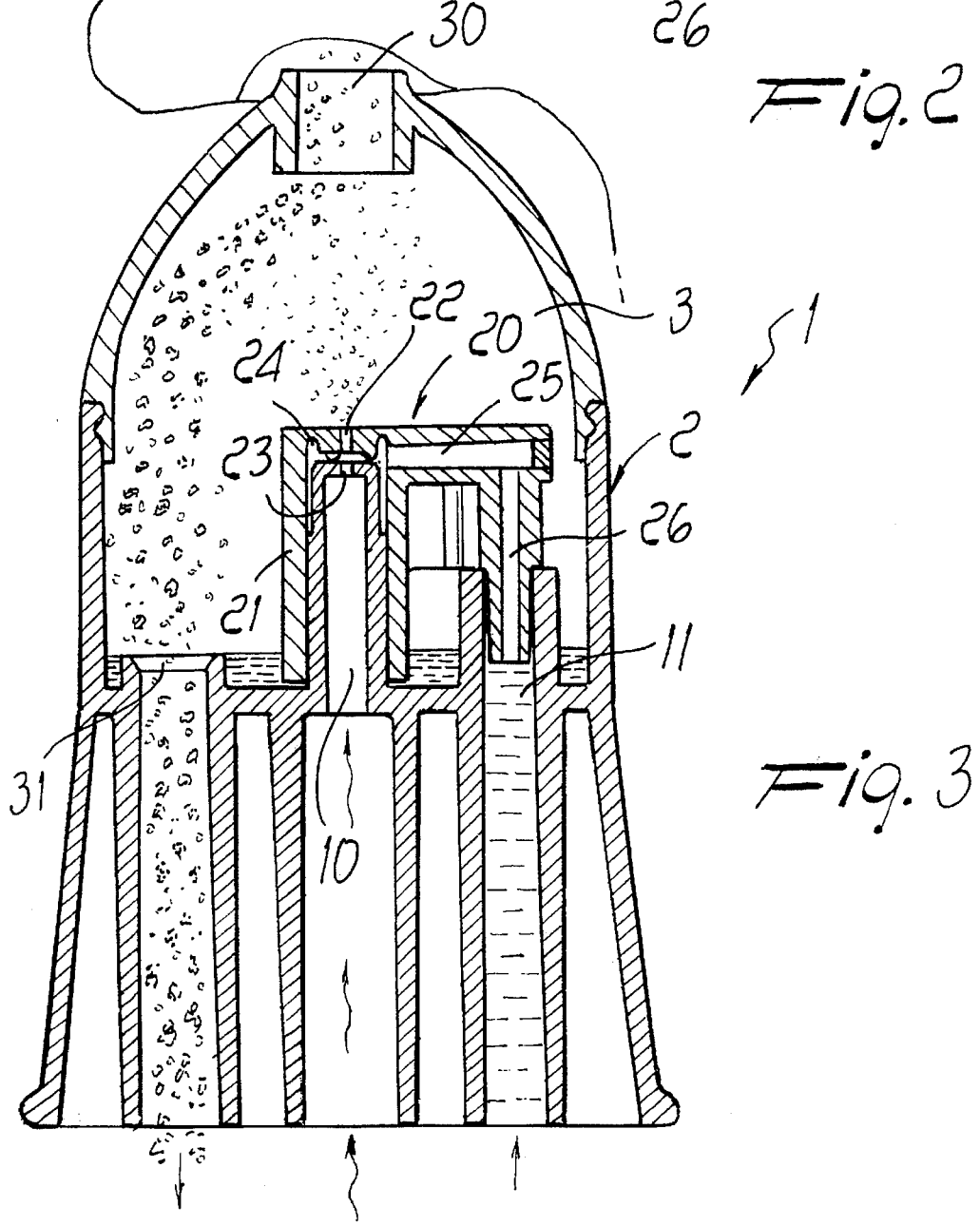
FIG. 3 is an enlarged-scale view of the micronized douche device of the previous figures.

The spray nozzle 22 is axially aligned with an outlet hole 30 for the atomized flow of the cleansing liquid, which is then introduced in the nasal fossae and in the neighboring regions, as seen for example in FIGS. 1 and 3, thus obtaining an effective cleansing action, in the manner described in the above-mentioned patent application.

A discharge port 31 is provided at the bottom of the atomization chamber 3 and allows the outward evacuation of the cleansing liquid with the removed secretions.

It is important to note that with this type of arrangement there is absolutely no mixing of the atomized cleansing liquid with the cleansing liquid that contains the removed secretions, which are directly expelled outwards.

In practical operation, the water particles, having a size of more than 10μ, enter the nasal cavities and, by virtue of the abundant distribution of the cleansing flow, can perform complete cleansing of the nasal cavity, of the rhinopharynx, and of the pharynx, as well as of the paranasal sinuses and of the middle ear, with a method already extensively described in the above-mentioned patent application.

From the above description it is thus evident that the invention achieves the intended aim and objects, and in particular, the fact is stressed that the connecting element that directly connects the injector to the cleansing liquid feed duct allows to provide two mutually separate circuits and more specifically a circuit for introducing and atomizing the cleansing liquid and a circuit for externally discharging the cleansing liquid with the removed secretions, thus allowing to perform an effective cleansing that always complies with optimum hygiene characteristics.

The invention thus conceived is susceptible of numerous modifications and variations, all of which are within the scope of the inventive concept.

All the details may furthermore be replaced with other technically equivalent elements.

In practice, the materials employed, as well as the contingent shapes and dimensions, may be any according to the requirements.

What is claimed is:

1. A micronized douche device for cleansing nasal and neighboring cavities, which comprises a bell-shaped body that forms an atomizing chamber, the device further comprising a spray nozzle associated with a duct for feeding a cleansing liquid and with a compressed air injector, said spray nozzle being axially aligned with a hole for the outflow of the atomized stream of cleansing liquid, a port for the discharge of the cleansing liquid, with the removed secretions, being also provided on the bottom of said atomization chamber, a connecting element joining said compressed air injector and said cleansing liquid feed duct so as to keep separate the cleansing liquid from the cleansing liquid with the removed secretions which is to be discharged.

2. A micronized douche device according to claim 1, wherein said connecting element has a sleeve-like portion that can be applied hermetically to said injector to form, proximate to the end that lies opposite to the open end of said sleeve, an annular chamber that is provided with said spray nozzle, a branching duct entering radially into said annular chamber and being connected to a coupling that is associable with said duct for introducing a cleansing liquid.

3. A micronized douche device according to claim 1, comprising a circuit for introducing the cleansing liquid that is separate from the circuit for externally expelling the cleansing liquid with the removed secretions.

4. A micronized douche device comprising:

an atomization chamber formed inside a body;

a compressed air injection duct;

a cleansing liquid duct;

a spray nozzle communicating with said atomization chamber and with said compressed air injection duct and said cleansing liquid duct such that said ducts only communicate with said chamber through said spray nozzle;

an outlet hole for releasing an atomized stream of cleansing liquid from said chamber;

a discharge port arranged distally from said spray nozzle for discharging liquid with removed secretions from said chamber; and a connecting element joining said compressed air injector duct and said cleansing liquid feed duct so as to keep separate the cleansing liquid from the cleansing liquid with the removed secretions which is to be discharged.

5. The device of claim 4, wherein said spray nozzle is axially aligned with said compressed air injection duct and with said outlet hole, and said cleansing liquid duct has a portion extending radially from the aligned axis of the spray nozzle substantially at a zone where said spray nozzle and said compressed air injection duct communicate.

6. The device of claim 4, wherein said spray nozzle is positioned in a central zone of said chamber and said discharge port is positioned at a bottom zone of said chamber.

* * * * *